United States Patent [19]

Willis et al.

[11] 4,267,111

[45] May 12, 1981

[54] PROCESS FOR PREPARING β-(3-EXO-HYDROXY-ENDO-2,3-DIMETHYL-2-NORBORNYL)-PROPIONIC ACID δ-LACTONE

[75] Inventors: Brian J. Willis, Bergenfield; Philip A. Christenson, Midland Park, both of N.J.; Derek H. R. Barton, Gif-sur-Yvette, France

[73] Assignee: Fritzsche Dodge & Olcott Inc., New York, N.Y.

[21] Appl. No.: 46,481

[22] Filed: Jun. 7, 1979

Related U.S. Application Data

[62] Division of Ser. No. 877,759, Feb. 14, 1978.

[51] Int. Cl.$^3$ .......................................... C07D 311/94
[52] U.S. Cl. ........................... 260/343.21; 260/345.3; 260/466; 560/120; 562/502; 568/820; 564/188; 585/357; 585/360
[58] Field of Search .................................. 260/343.21

[56] References Cited

U.S. PATENT DOCUMENTS

| | | | |
|---|---|---|---|
| B 491,032 | 2/1976 | Skorianetz | 260/343.21 |
| 3,673,261 | 6/1972 | Kretschmar et al. | 568/820 |
| 3,679,756 | 7/1972 | Kretschmar et al. | 568/820 |
| 3,927,116 | 12/1975 | Rick et al. | 568/820 |
| 4,159,258 | 6/1979 | Ohloff et al. | 260/343.21 |

OTHER PUBLICATIONS

Herout et al., Chem. Abst. 51, 1957, 296d.
Gream et al., Tetrahedron, vol. 22, pp. 2583–2597, 1966.

*Primary Examiner*—Henry R. Jiles
*Assistant Examiner*—Jane T. Fan
*Attorney, Agent, or Firm*—Cooper, Dunham, Clark, Griffin & Moran

[57] ABSTRACT

This invention concerns processes for preparing β-santalol, β-santalene, dihydro-β-santalol, tetrahydro-β-santalol and related compounds from camphene. The invention further concerns novel compounds useful as intermediates in these processes and as fragrance adjuncts.

7 Claims, No Drawings

PROCESS FOR PREPARING β-(3-EXO-HYDROXY-ENDO-2,3-DIMETHYL-2-NORBORNYL)-PROPIONIC ACID δ-LACTONE

This is a division, of application Ser. No. 877,759 filed Feb. 14, 1978.

BACKGROUND OF THE INVENTION

Each Indian sandalwood oil is used in large quantities by the perfume industry. High prices and a sometimes sporadic supply of the oil have encouraged research chemists to develop syntheses of various components of the oil. One of the major components of the oil is β-santalol which is known to possess a desirable sandalwood odor. Cis-β-santalol is shown as structure I, wherein R=—CH$_3$. Trans-β-santalol is shown as structure IV, wherein R=—CH$_3$. β-Santalene, shown as structure II, wherein R=R$^1$=—CH$_3$, and dihydro β-santalol, shown as structure III, wherein R=—CH$_3$, are known minor components of East Indian sandalwood oil.

U.S. Pat. No. 3,662,008 describes a process for preparing β-santalol from 3-methylnorcamphor. The present invention describes novel processes for preparing β-santalene, cis- and trans-β-santalol, dihydro-β-santalol, tetrahydro-β-santalol (structure V, wherein R=—CH$_3$), and related compounds from camphene, structure VI.

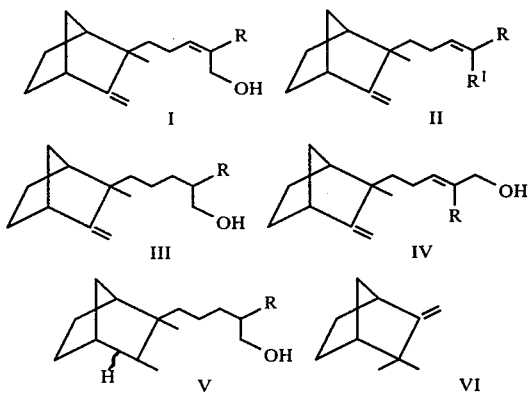

SUMMARY OF THE INVENTION

One object of the present invention is to provide a process for preparing β-santalene and related compounds. This novel process comprises the following steps:

(1) preparing β-(2-exo-hydroxy-3,3-dimethyl-2-norbornyl)-propionic acid γ-lactone and its endo isomer from camphene;

(2) treating the product of Step (1) with an acid to cause rearrangement to β-(3-exo-hydroxy-endo-2,3-dimethyl-2-norbornyl)-propionic acid δ-lactone;

(3) reducing the product of Step (2) with a metal hydride to form β-(3-exo-hydroxy-endo-2,3-dimethyl-2-norbornyl)-propanal-hemiacetal;

(4) reacting the product of Step (3) with an alkylidene trisubstituted phosphorane; and (5) dehydrating the product of Step (4) so as to produce said compounds.

Another object of the invention is to provide a process for preparing cis-β-santalol and related compounds. This process comprises the following steps:

(1) preparing β-(2-exo-hydroxy-3,3-dimethyl-2-norbornyl)-propionic acid γ-lactone and its endo isomer from camphene;

(2) treating the product of Step (1) with an acid to cause rearrangement to β-(3-exo-hydroxy-endo-2,3-dimethyl-2-norbornyl)-propionic acid δ-lactone;

(3) converting the product of Step (2) to β-(2-endo-methyl-3-methylene-2-norbornyl)-propanal; and (4) reacting the product of Step (3) with an alkylidene trisubstituted phosphorane, followed by treatment with a strong base and then with formaldehyde so as to produce said compounds.

It is a still further object of the invention to provide a process of preparing trans-β-santalol and related compounds. This process comprises the following steps:

(1) preparing β-(2-exo-hydroxy-3,3-dimethyl-2-norbornyl)-propionic acid γ-lactone and its endo isomer from camphene;

(2) treating the product of Step (1) with an acid to cause rearrangement to β-(2-exo-hydroxy-endo-2,3-dimethyl-2-norbornyl)-propionic acid δ-lactone;

(3) converting the product of Step (2) to β-(2-endo-methyl-3-methylene-2-norbornyl)-propanal;

(4) reacting the product of Step (3) with an anion having the formula R-⊖CPO(OR$^2$)$_2$ CO$_2$R$^1$ wherein R is H or lower alkyl and R$^1$ and R$^2$ are lower alkyl in order to produce an unsaturated ester; and (5) reducing the ester with a metal hydride so as to prepare said compounds.

It is another object of the invention to provide a process for preparing dihydro-β-santalol and related compounds which comprises preparing unsaturated esters according to Steps (1)–(4) of the process for preparing trans-β-santalol and related compounds and then reducing the esters with a metal hydride.

It is yet another object of the invention to provide a process for preparing tetrahydro-β-santalol which comprises preparing the compound cis-β-santalol or the compound trans-β-santalol or a mixture thereof and catalytically hydrogenating the compound or mixture.

A still further object of this invention is to provide new compounds useful as intermediates in the processes of this invention and as fragrance adjuncts.

A final object of this invention is to provide fragrance compositions which comprise the novel compounds described herein in an effective amount to impart fragrance thereto.

At least one of the above objects will be achieved in at least one of the embodiments of this invention as described more fully in the detailed description of the invention and claims which follow.

DETAILED DESCRIPTION OF THE INVENTION

Camphene (VI) can be converted to β-(2-exo-hydroxy3,3-dimethyl-2-norbornyl)-propionic acid γ-lactone and its endo isomer (VII) by several methods. Reaction of camphene with manganese triacetate or with haloacetic acids, e.g. chloroacetic acid, in the presence of alkali metal halides, e.g. potassium bromide, provides lactone (VII) directly.

Alternatively, camphene (VI) can be oxidized to form 3,3-dimethyl-2-methyloxa-cyclopropane-bicyclo-[2.2.1]-heptane (camphene epoxide, (VIII)) and the epoxide then reacted with an anion which includes a group which allows formation of a lactone or imino-lactone type bridge, e.g. groups such as —$CO_2C_2H_5$, —$CO_2CH_3$, and —CN, so as to finally produce VII.

Thus, peracid, e.g. peracetic acid, oxidation of camphene (VI) provides camphene epoxide (VIII) as a mixture of exo and endo isomers. Reaction of VIII with anions having the formula $\ominus CH_2(XY)$ wherein Y is a group allowing formation of a lactone or imino-lactone type bridge and X is hydrogen or easily removable group, e.g. —$CO_2C_2H_5$, provides the intermediate lactone IX which can be converted to VII. For example, $\ominus CH(CO_2C_2H_5)_2$ gives IX (wherein Y=—$CO_2C_2H_5$) which, upon heating with moist dimethyl sulfoxide (DMSO), gives VII. Also, anions having the formula $\ominus CH_2Y$, wherein Y is a group allowing formation of a lactone or imino-lactone type bridge, react with VIII to provide VII. For example, $\ominus CH_2CO_2\ominus$, generated from acetic acid upon treatment with a strong base, e.g. lithium diethylamide, reacts with VIII to yield VII.

These reactions can be shown schematically as follows:

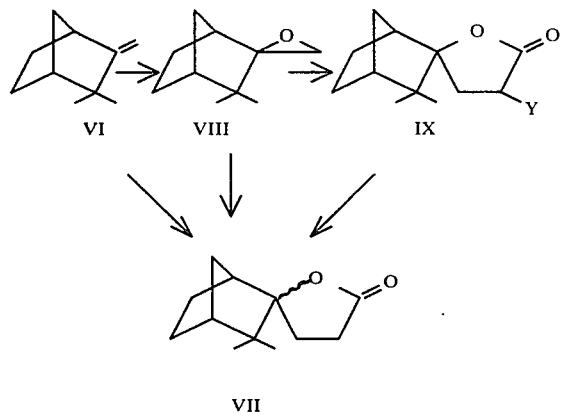

Lactone VII rearranges to β-(3-exo-hydroxy-endo-2,3-dimethyl-2-norbornyl)-propionic acid δ-lactone (X) upon treatment with acids including proton-yielding acids, e.g. formic acid, perchloric acid, trifluoroacetic acid, sulfuric acid, polyphosphoric acid and hydrochloric acid, and Lewis acids, e.g. stannic chloride and boron trifluoride etherate. Thus,

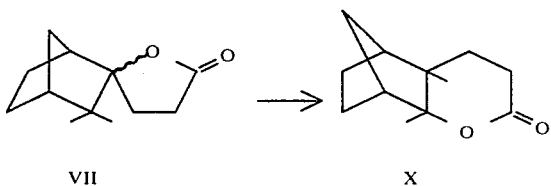

Lactone X can be readily converted to β-santalene (II, wherein R=$R^1$=—$CH_3$) and its related compounds (II, wherein R and $R^1$ are H or lower alkyl, i.e. having 4 carbon atoms or less). Reduction of X with a metal hydride, e.g. diisobutylaluminum hydride or lithium triethoxyaluminum hydride, yields β-(3-exo-hydroxy-endo-2,3-dimethyl-2-norbornyl)-propanal-hemi-acetal (XI). Reaction of XI with an alkylidene trisubstituted phosphorane, e.g. isopropylidene triphenylphosphorane, yields an endo-2,3-dimethyl-exo-2-(3-alkenyl)-exo-3-hydroxy-bicyclo-[2.2.1]-heptane (XII, wherein R and $R^1$ are H or lower alkyl). Alcohols XII upon reaction with a dehydrating agent, e.g. thionyl chloride or phosphorous oxychloride, in pyridine yield II.

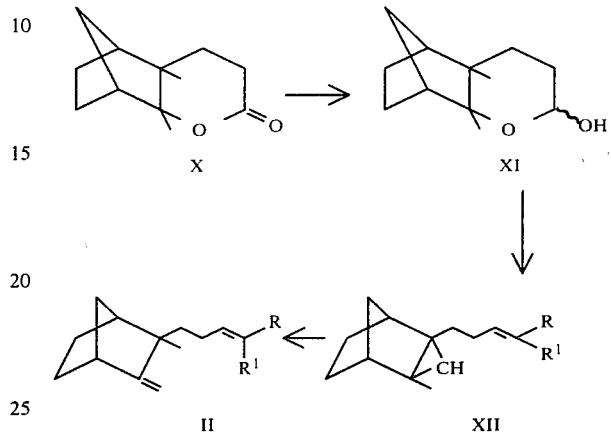

In order to prepare β-santalene (II, wherein R=$R^1$=—$CH_3$), XI is reacted with isopropylidene triphenylphosphorane, generated by reacting an isopropyltriphenylphosphonium halide with a strong base, e.g. dimsyl sodium, to prepare XII, wherein R=$R^1$=—$CH_3$ and XII is dehydrated to yield β-santalene.

Alternatively, lactone X can be converted to β-(2-endo-methyl-3-methylene-2-norbornyl)-propanal (XIII) by two routes. Transesterification and dehydration of X to yield lower alkyl β-(2-endo-methyl-3-methylene-2-norbornyl)-propionate (XIV) is accomplished by treatment with a lower alkyl alcohol in a solvent, e.g. benzene, containing an acid catalyst, e.g. p-toluenesulfonic acid, boron trifluoride etherate, sulfuric acid or a cationic exchange resin. Metal hydride, e.g. diisobutylaluminum hydride, reduction of ester XIV provides aldehyde XIII.

In addition, aminolysis of X yields β-(3-exohydroxy-endo-2,3-dimethyl-2-norbornyl)-propionamide (XV) which is dehydrated to β-(endo-2-methyl-3-methylene-2-norbornyl)-propionitrile (XVI). Reduction of XVI with a metal hydride, e.g. diisobutylaluminum hydride, provides aldehyde XIII.

This series of reactions can be depicted as follows:

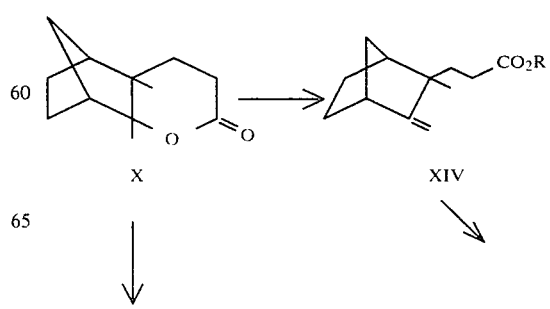

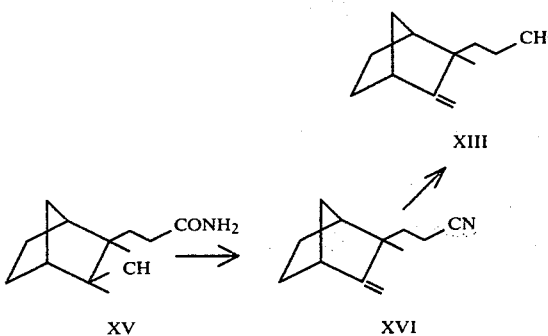

Aldehyde XIII can be converted to cis-β-santalol I, wherein R=—CH₃) or its related compounds, (I, wherein R is H or lower alkyl, i.e. has 4 carbon atoms or less). Aldehyde XIII can also be converted to trans-β-santalol (IV, wherein R=—CH₃) and its related compounds (IV, wherein R is H or lower alkyl, i.e. has 4 carbon atoms or less).

To prepare compounds having the structure I, wherein R is H or lower alkyl, aldehyde XIII is reacted with an alkylidene trisubstituted phosphorane followed by treatment of the resulting product with a strong base, and then with formaldehyde. Thus, to prepare cis-β-santalol (I, wherein R=—CH₃), XIII is reacted with ethylidene triphenylphosphorane, followed by sequential treatment with a strong base, e.g. n-butyl lithium, then with formaldehyde.

To prepare compounds having the structure IV, wherein R is H or lower alkyl, aldehyde XIII is reacted with an anion having the formula R-⊖CPO(OR²)₂CO₂R¹, wherein R is H or lower alkyl and R¹ and R² are lower alkyl so as to produce an unsaturated ester having the structure XVII. Reduction of the ester with a metal hydride yields the desired compounds IV. Thus, to prepare trans-β-santalol (IV, wherein R is —CH₃), XIII is reacted with the anion of triethyl α-phosphonopropionate. This yields ethyl 5-(2-endo-methyl-3-methylene-2-norbornyl)-2-methyl-trans-2-pentenoate (XVII, wherein R =—CH₃ and R¹=—C₂H₅). Reduction with a metal hydride, e.g. lithium aluminum hydride, or aluminum hydride, yields trans-β-santalol.

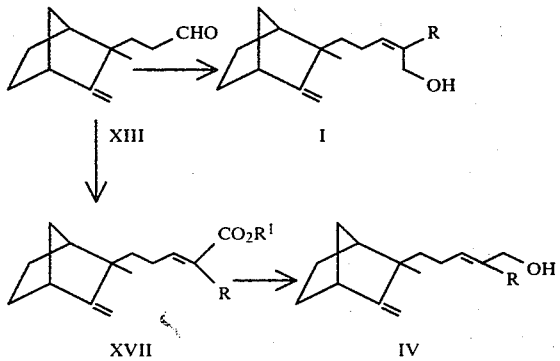

Trans esters XVII or a mixture of cis and trans esters may be converted to dihydro β-santalol or related compounds by metal hydride reduction of XVII with, e.g. lithium aluminum hydride. Thus,

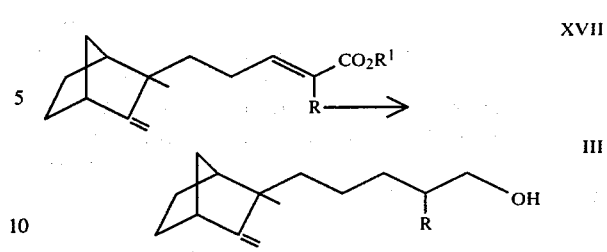

Cis-β-santalol and its related compounds (I), trans-β-santalol and its related compounds (IV) or a mixture of the two can be converted to tetrahydro compounds (V, wherein R is H or lower alkyl) by catalytic hydrogenation of I, IV or a mixture of the two, e.g. over platinum oxide/sodium nitrile.

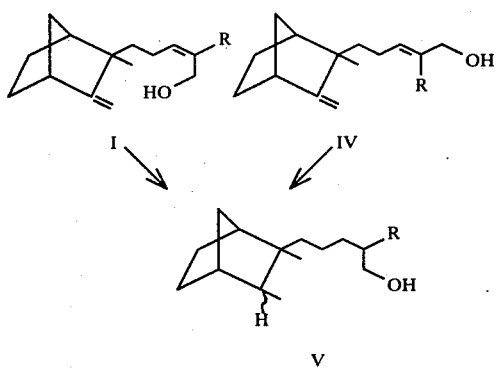

Compounds X, XI, XIV, XV and XVI are novel compounds. They are useful as intermediates in the processes of the invention. Additionally, each of these new compounds has a characteristic fragrance rendering these compounds useful as fragranch adjuncts either alone or in compositions, e.g. perfume compositions, containing an effective amount of the compounds to impart fragrance thereto, e.g. an amount in the range from about 0.1 to about 50% by weight, usually an amount in the range 0.5–30% by weight.

Compound X is characterized by a weak, buttery odor with woody undertones; compound XI by a weak woody odor; compound XIV by a woody odor reminiscent of qualacwood and sandalwood; compound XV by a weak woody odor; and compound XVI by a strong green, floral and fruity odor.

The following examples are set forth to more fully define and illustrate the processes of the invention but are not intended in any way to limit its scope.

EXAMPLE 1

Peracetic acid (114 g. of a 40% solution, saturated with sodium acetate) was added to a mixture of camphene (102 g.) and sodium carbonate (127.2 g.) in methylene chloride (900 ml.) with cooling such that the temperature was between 5° and 25°.

After six hours, aqueous work-up, extraction with methylene chloride and evaporation of the solvent gave 99.11 g. of a solid. Analysis by NMR (CDCl₃) δ0.87 (6H,s,>C(CH₃)₂), 2.63 and 2.73

(2H, 2s, ).

0.8–2.1 (8H,m) and IR (CCl$_4$)νmax 2940,1545,1460 cm$^{-1}$ identified the product as 3,3-dimethyl -2-methyloxa-cyclopropane-bicyclo-[2.2.1]-heptane (camphene epoxide) having the structure:

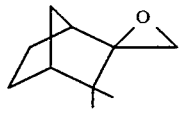

(VIII)

EXAMPLE 2

To a mixture of benzene (160 ml.), hexamethylphosphoramide (165 ml.) and diethylamine (88 ml.) was added lithium shot (5.91 g.) and the mixture was stirred with cooling in a water bath until all the lithium had dissolved. Tetrahydrofuran (200 ml.) was added and the solution cooled in an ice bath. Acetic acid (25.6 g.) dissolved in tetrahydrofuran (50 ml.) was added gradually. The reaction mixture was then heated at 30° to 45° for 0.5 hour. Camphene epoxide (56.06 g.) dissolved in benzene (20 ml.) was slowly added to the reaction mixture.

After refluxing for 22 hours, the solution was poured into ice water and the product was extracted into aqueous base which was then acidified with sulfuric acid. Extraction with benzene, evaporation of the solvent and crystallization from petroleum ether gave 26.57 g. of crystals m.p. 101°–2°. Analysis by NMR (CDCl$_3$) δ0.95 and 0.98

(6H,2s, 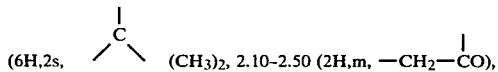 (CH$_3$)$_2$, 2.10–2.50 (2H,m, —CH$_2$—CO), 0.95–2.10 (10H,m), and IR (CHCl$_3$) νmax 2940, 1760 cm$^{-1}$ identified the product as β-(α-exo-hydroxy-3,3-dimethyl-2-norbornyl)-propionic acid γ-lactone and its endo isomer having the structure:

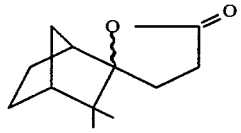

(VII)

EXAMPLE 3

Sulfuric acid (500 ml.) was cooled to −10° in an ice-methanol bath. Then a mixture of β-(2-exo-hydroxy-3,3-dimethyl-2-norbornyl)-propionic acid-γ-lactone and its endo isomer (25 g.) was added and the mixture stirred vigorously for 45 minutes. Work-up provided 11.8 g. of starting material and 9.9 g. of δ-lactone m.p. 90°–92°. NMR (CDCl$_3$) δ1.02

(3H,s, 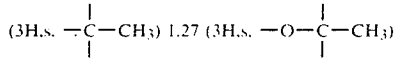) 1.27 (3H,s, —O—C(—CH$_3$)

IR (CDCl$_3$) νmax. 1735 cm$^{-1}$ MS (m/e) 194,179,166,151. Analysis: Calcd. for C$_{12}$H$_{18}$O$_2$; C; 74.19,H;9.34. Found: C;74.07, H; 9.28. This indicated that the product was β-(3-exo-hydroxy-endo-2,3-dimethyl-2-norbornyl)-propionic acid-δ-lactone having the structure:

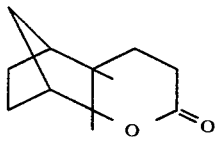

(X)

EXAMPLE 4

To a solution of β-(3-exo-hydroxy-2,3-dimethyl-2-morbornyl)-propionic acid-δ-lactone (0.58 g.) in toluene (50 ml.) was added dropwise diisobutylaluminum hydride (0.85 g.) in toluene (4.3 ml.). After 1.25 hours, the reactants were poured into a solution of acetic acid in ice water (30 ml.) and the mixture stirred vigorously for 0.5 hour. Extraction with toluene and evaporation of solvent yielded 0.60 g. of the lactol. NMR (CDCl$_3$) δ0.90 (3H,s,—CH$_3$), 1.30

(3H,s, 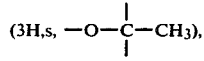), 3.95 (1H,broad s,—OH), 5.15–5.48 (1H,t,>CH-OH). IR (CHCl$_3$) νmax 3300,2950 cm$^{-1}$. MS (m/e) 196,178,153. Analysis: Calcd. for C$_{12}$H$_{20}$O$_2$; C;73.42,H;10.27. Found: C;73.82,H;10.45. This identified the product as β-(3-exo-hydroxy-endo-2,3-dimethyl-2-norbornyl)-propanal-hemi-acetal having the structure:

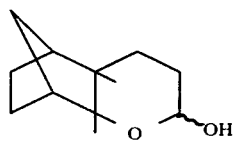

(XI)

EXAMPLE 5

Sodium hydride (0.053 g., free of mineral oil) was suspended in dimethyl sulfoxide (5 ml.) and the mixture heated to 50°–70° until all of the sodium hydride was reacted. Then the solution was cooled and isopropyltriphenylphosphonium iodide (0.951 g.) was added. Ater 0.25 hour at 25°, β-(3-exo-hydroxy-2,3-dimethyl-2-norbornyl)-propanal-hemi-acetal (0.196 g.) was added. After heating for 42 hours at 50°–55°, the reactants were poured into water and extracted with petroleum ether. Evaporation of the solvent and distillation of the residue afforded 0.195 g. of an oil, b.p. 95°–108°, 0.3 mm. NMR (CDCl$_3$) δ0.88

(3H,s, —C̶—CH₃), 1.18(3H,s, —C̶(OH)—CH₃), 1.60 and

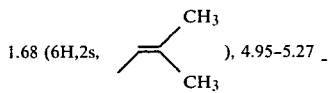
1.68 (6H,2s, ), 4.95-5.27

0.9-2.6 (13H,m) IR (film) νmax 3450,2950,1420 cm⁻¹. MS (m/e) 222,204,179. This identified the product as endo-2,3-dimethyl-exo-2-(4-methyl-3-pentenyl)-exo-3-hydroxy-bicyclo [2.2.1] heptane having the structure:

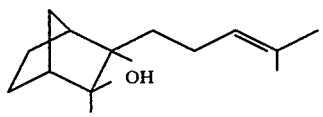

(XII, wherein R = R¹ = CH₃)

EXAMPLE 6

To a solution of phosphorous oxychloride (0.3 ml.) in pyridine (2.2 ml.) cooled in an ice bath was added endo-2,3-dimethyl-exo-2-(4-methyl-3-pentenyl)-exo-3-hydroxy-bicyclo [2.2.1] heptane (0.170 g.) in pyridine (1.5 ml.). After stirring for 17 hours, the solution was poured into ice water and extracted with ether. Evaporation of the solvent and distillation of the residue gave 0.111 g. of an oil. b.p. 105°–110°, 5 mm. NMR (CCl₄)δ1.03 (3H,s,—CH₃) 1.59 and 1.65

(6H,2s, ⋀(CH₃)₂) 2.53-2.75 (1H,m,—CH—⟨ ), 4.43 and 4.69 (2H,2s, ⟩=CH₂), 4.87-5.26 (1H,m, —CH ⟨ )

1.0-2.2 (11H,m). IR (film) νmax 2980,1660,1460 cm⁻¹, MS (m/e) 204,189,161,122,94. This identified the product as endo-2-methyl-exo-2-(4-methyl-2-pentenyl)-3-methylene-bicyclo-[2.2.1]-heptane (β-Stantalene) having the structure

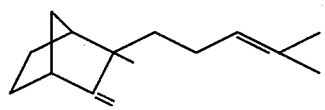

(II, wherein R = R¹ = —CH₃)

EXAMPLE 7

A mixture of β-(3-exo-hydroxy-2,3-dimethyl-2-norbornyl)-propionic acid-δ-lactone (9.00 g.), p-toluenesulphonic acid (0.45 g.), ethanol (200 ml.) and benzene (150 ml.) was refluxed through a Soxhlet extractor containing sodium sulfate for 75 hours. Aqueous work up and extraction with benzene, followed by evaporation of the solvents and distillation of the residue gave the ester (7.11 g.) b.p. 105°–107°, 1.2 mm. NMR (CDCl₃) δ1.03

(3H,s,—C̶—CH₃).

1.1-1.4 (3H,t,J-7 Hz —CH₂-C̲H̲₃), 3.95-4.3 (2H,q, J=7 Hz, -C̲H̲₂-CH₃), 4.53 and 4.80

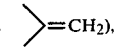
(2H,2s ⟩=CH₂), 2.57-2.78 (1H,m,—CH-≦), 1.0-2.45 (11H,m). IR (film) νmax 2940,1735,1650 cm⁻¹. MS (m/e) 222,207,194,193,177. Analysis: Calcd. for C₁₄H₂₂O₂: C;75.63,H;9.98. Found: C;75.69 H;9.98. This identified the product as ethyl β-(2-endo-methyl-3-methylene-2-norbornyl)propionate having the structure

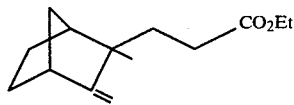

(XIV, wherein R = C₂H₅)

EXAMPLE 8

A mixture of β-(3-exo-hydroxy-endo-2,3-dimethyl-2-norbornyl)-propionic acid-δ-lactone (0.40 g.), ammonia (12 g.), ammonium chloride (0.1 g.) and methanol (10 ml.) was heated in a sealed reaction vessel at 100° for 94 hours. After cooling and partial removal of solvents, the reaction mixture was poured into water and extracted with chloroform. Evaporation of solvents, and crystallization from benzene/petroleum ether gave 0.27 g. of the amide, m.p. 109°–110°. NMR (CDCl₃) δ0.83

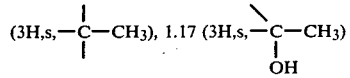
(3H,s,—C̶—CH₃), 1.17 (3H,s,—C̶—CH₃)
　　　　　　　　　　　　　　　　　 OH 0.90-2.55 (12H,m), 2.25 (1H, broad s, —OH, exchanges with D₂O), 5.6-6.4 (2H, broad s,—NH₂, exchanges slowly with D₂O). IR (CHCl₃)ν max 3350, shoulder at 3500,2980,1660,1600 cm⁻¹. MS (m/e) 211,193. Analysis: Calcd. for C₁₂H₂₁NO₂: C;68.21,H;10.02,N;6.63. Found: C;68.08,H;9.91,N;6.57. This identified the product as β-(3-exo-hydroxy-endo-2,3-dimethyl-2-norbornyl)-propionamide having the structure

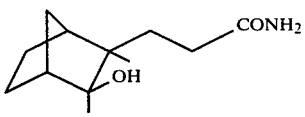

(XV)

EXAMPLE 9

A mixture of β-(3-exo-hydroxy-endo-2,3-dimethyl-2-norbornyl)-propionamide (0.74 g.) p-toluenesulfonyl chloride (2.67 g.) and pyridine (40 ml.) was heated at 90°–100° for 21 hours. After cooling, the reactants were poured into water and extracted with ether. Evaporation of solvents and distillation of the residue gave 0.551 g. of the nitrile. b.p. 73°–76°, 0.5 mm. NMR (CDCl₃) $\delta$1.05 (3H,s,—CH₃), 1.0–2.6 (11H,m), 2.63–4.53 (1H,m,—CH—≦) 4.48 and 4.83

(2H,2s, >=CH₂).

IR (film) νmax 2960,2250,1660 cm⁻¹. MS (m/e) 175,160,146. Analysis: Calcd. for $C_{12}H_{17}N$: C;82.23,H;9.78. Found C;82.00,H;9.80. This identified the product as β-(endo-2-methyl-3-methylene-2-norbornyl)-propionitrile having the structure

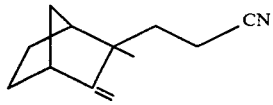

(XVI)

EXAMPLE 10

To a solution of β-(endo-2-methyl-3-methylene-2-norbornyl)-propionitrile (0.123 g.) in hexane (12 ml.) cooled to −78° was added diisobutylaluminum hydride (0.84 ml. of a 1 M solution in hexane) gradually. After stirring for 1 hour at −78° and 0.5 hours at 0°, ether (15 ml.) and 10% acetic acid solution (10 ml.) was added and the mixture stirred at 25° for 0.75 hours. After extraction with petroleum ether (60°–90°), evaporation of solvents and distillation of the residue, there was obtained 0.109 g. of the aldehyde b.p. 78°–79° 1 mm, β-(2-endo-methyl-3-methylene-2-norbornyl)-propanol having the structure

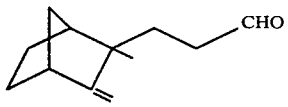

(XIII)

EXAMPLE 11

To a solution of ethyl β-(2-endo-methyl-3-methylene-2-norbornyl)-propionate (1.25 g.) in toluene (75 ml.) cooled to −78° was added diisobutylaluminum hydride (5.6 ml. of a 1 M solution in hexane) gradually. After stirring in the cold for 3 hours additional diisobutylaluminum hydride solution (0.6 ml.) was added and after 20 minutes the mixture was poured into 5% acetic acid solution (30 ml.). Extraction with toluene, evaporation of solvents, and distillation of the residue gave 0.90 g. b.p. 78°–79°, 1 mm. NMR (CCl₄) $\delta$1.01 (3H, s, —CH₃) 1.0–2.6 (11H, m) 2.6–2.80

(1H,m,—CH—<) 4.45 and 4.75 (2H,2s, >=CH₂)

9.68–9.62 (1H, t., J=2 Hz). IR (film) νmax 2940, 2700, 1725 cm⁻¹. MS (m/e) 178, 163, 160, 145. This identified the product as Δ-(2-endo-methyl-3-methylene-2-norbornyl)-propanal having the structure

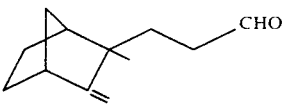

(XIII)

EXAMPLE 12

To a suspension of ethyl triphenylphosphonium bromide (1.436 g.) in tetrahydrofuran (10 ml.) was added n-butyl lithium (1.7 ml. of a 2.3 M solution in hexane). After 15 minutes, the solution was cooled to −78° and β-(2-endo-methyl-3-methylene-2-norbornyl)-propanal (0.709 g.) in tetrahydrofuran (8 ml.) was added dropwise. After 5 minutes at −78°, n-butyl lithium (2.3 ml. of 2.3 M solution in hexane) was added gradually. After stirring for 20 minutes at −78°, the solution was placed in an ice bath and excess formaldehyde was added. Next day, the reaction mixture was poured into saturated ammonium chloride solution (40 ml.) and extracted with ether. Work-up and distillation of the residue gave 0.384 g. of β-santalol b.p. 110°–120°, 0.3 mm. NMR (CCl₄) $\delta$1.05

(3H,s,—C(CH₃)—CH₃), 1.73 (3H, broad s, =<CH₃/—OH), 1.0–1.90 (9H,m) 1.95–2.3 (3H,m,CH₂=<) and —OH bridehead proton) 2.60–2.75 (1H,m,—CH/\)

4.06 (2H,s,—CH₂—OH) 4.62 and 4.90 (2H,2s, >=CH₂)

IR (film) νmax 3330, 2940, 1660 cm⁻¹, MS (m/e) 220, 202, 187. This identified the product as 5-(2-endo-methyl-3-methylene-2-norbornyl)-2-methyl-cis-2-benten-1-ol (cis β-Santalol) having the structure

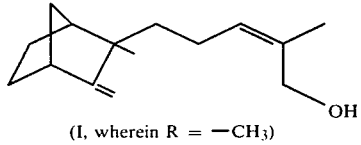

(I, wherein R = —CH₃)

EXAMPLE 13

To a suspension of sodium hydride (0.063 g. free of mineral oil) in dimethoxyethane (15 ml.) was added triethyl α-phosphonopropionate (0.624 g.) in dimethyoxyethane (1 ml.). After the reaction with sodium hydride was complete, the solution was cooled to 0° and β-(2-endo-methyl-3-methylene-2-norbornyl)-propanal (0.591 g.) in dimethoxyethane (1 ml.) was added gradually. After 1 hour at 25° and 0.5 hours at 70°, the reaction mixture was poured into water and extracted with ether. Work-up and distillation of the residue gave 0.636 g. of the ester b.p. 120°–130° 0.3 mm. NMR (CCl₄) $\delta$1.02

(3H,s,—C̲—CH₃), 1.01-1.28 (3H,t,J = 7Hz,—CH₂—CH₃),

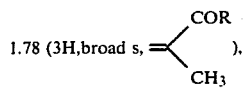
1.78 (3H,broad s, 1.0-2.4 (11H,m), 2.55-2.80 (1H,m,—CH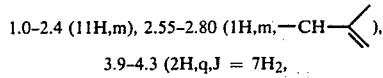), 3.9-4.3 (2H,q,J = 7H₂, —CH₂—CH₃), 4.43 and 4.70 (2H,2s, 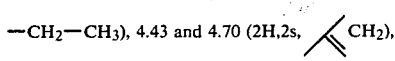), 6.43-6.84 (1H,m, 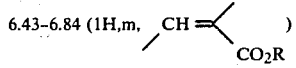)

IR (film) νmax 2980, 1705, 1650, 1475 cm⁻¹. This identified the product as ethyl 5-(2-endo-methyl-3-methylene-2-norbornyl)-2-methyl-trans-2-pentenoate having the structure

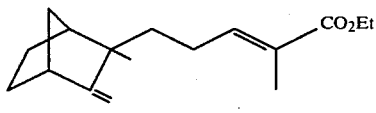

(XVII, wherein R = CH₃ and R¹ = —C₂H₅)

EXAMPLE 14

To a solution of aluminum chloride (0.184 g.) in ether (20 ml.) cooled to 0° was added lithium aluminum hydride (0.158 g.). After 15 minutes, a solution of ethyl 5-(2-endo-methyl-3-methylene-2-norbornyl)-2-methyl-trans-2-pentenoate (0.545 g.) in ether (1.5 ml.) was added. After 45 minutes at 0°, the reactants were poured into 3 N HCl (20 ml.) and extracted with ether. Work-up and distillation of the residue gave 0.381 g. of trans-β-santalol b.p. 125°-130°, 0.3 mm. NMR (CCl₄) δ1.03

(3H,s,—C̲—CH₃), 1.62 (3H,broad s, 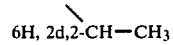), 1.0-2.3 (12H,m), 2.55 -2.78 (1H,m, 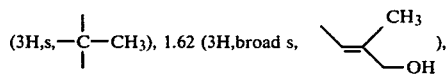) 3.85 (2H,s,—CH₂—OH) 4.43 and 4.70 (2H,2s, 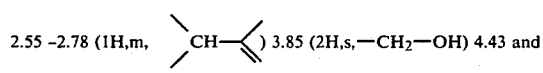) 5.1-5.5 (1H,m,—CH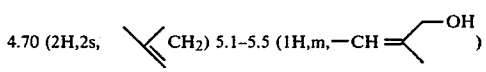)

IR (film) νmax 3330, 2960, 1660 cm⁻¹. This identified the product as 5-(2-endo-methyl-3-methylene-2-norbornyl)-2-methyl-trans-2-penten-1-ol (trans-β-santalol) having the structure

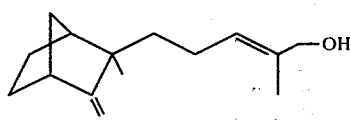

(IV, wherein R = —CH₃)

EXAMPLE 15

A mixture of trans-β-santalol (0.289), platinum oxide (0.050 g.), sodium nitrite (0.002 g.) and ethanol (10 ml.) was shaken under a hydrogen atmosphere for 20 hours. Filtration, evaporation of solvent and work-up gave tetrahydro-β-santalol (0.257 g.). NMR (CCl₄) δ0.73 (3H, s, —CH₃), 0.83 and 0.93

6H, 2d,2-CH—CH₃

0.75-2.3 (17H, m), 3.25-3.53 (2H, d, —C̲H̲₂—OH). IR (film) νmax 3550, 2940, 1460 cm⁻¹. MS (m/e) 224, 195, 177, 123. This identified the product as 5-(2-endomethyl-3-methyl-2-norbornyl)-2-methyl-2-pentan-1-ol (tetrahydro-β-santalol) having the structure

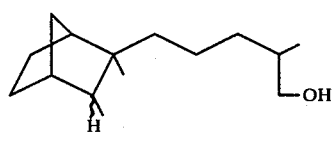

(V, wherein R = CH₃)

EXAMPLE 16

To a suspension of lithium aluminum hydride (0.080 g) in dimethoxyethane (10 ml) was added ethyl 5-(2-endo-methyl-3-methylene-2-norbornyl)-2-methyl-trans-2-pentenoate (0.25 g) in dimethoxyethane (3 ml) and the mixture was refluxed. Water (0.1 ml), 30% sodium hydroxide solution (0.1 ml) and water (0.3 ml) was added sequentially. Filtration, evaporation of solvents and work-up gave dihydro-β-santalol. NMR (CCl₄) δ1.03 (3H, s, —CH₃), 0.90-0.92 (3H, d, J=7 Hz, —CH—CH₃), 3.1-3.7 (2H, dd, J₁=7 Hz, J₂=4 Hz, —C̲H̲₂—OH), 2.55-2.75

(1H, m, ), 0.85-2.4 (12H, m), 4.42 and 4.70 (2H, 2s, >=CH₂). IR (film) νmax 3350, 2960, 1660 cm⁻¹. This identified the product as 5-(2-endo-methyl-3-methylene-2-norbornyl)-2-methyl-pentan-1-ol. (Dihydro-β-santalol) having the structure

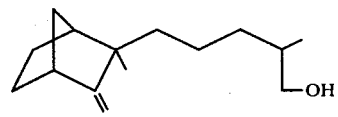

(III, wherein R = —CH₃)

As will be obvious to one skilled in the art, many modifications, variations, and alterations are possible in the practices of the invention without departing from the spirit and scope thereof.

We claim:

1. A method of preparing β-(3-exo-hydroxy-endo-2,3-dimethyl-2-norbornyl)-propionic acid δ-lactone which comprises treating β-(2-exo-hydroxy-3,3-dimethyl-2-norbornyl)-propionic acid γ-lactone and its endo isomer with an acid capable of effecting rearrangement under suitable conditions of temperature and time.

2. A process of preparing compounds of the structure

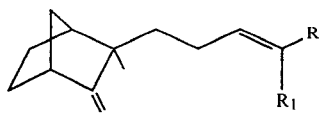

wherein R and R₁ may be hydrogen or lower alkyl which comprises:
(a) preparing β-(3-exo-hydroxy-endo-2,3-dimethyl-2-norbornyl)-propionic acid δ-lactone by the process of claim 1;
(b) reducing the product of step (a) with a metal hydride to form β-(3-exo-hydroxy-endo-2,3-dimethyl-2-norbornyl)-propanal-hemi-acetal;
(c) reacting the product of step (b) with an alkylidene trisubstituted phosphorane; and
(d) dehydrating the product of step (c) to form said compounds.

3. A process of preparing compounds of the structure

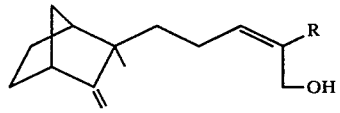

wherein R is hydrogen or lower alkyl which comprises:
(a) preparing β-(3-exo-hydroxy-endo-2,3-dimethyl-2-norbornyl)-propionic acid δ-lactone by the process of claim 1;
(b) converting the product of step (a) to β-(2-endo-methyl-3-methylene-2-norbornyl)-propanal by treating said product with a lower alkyl alcohol in a solvent containing an acid catalyst to transesterify and dehydrate said product to lower alkyl β-(2-endo-methyl-3-methylene-2-norbornyl)-propionate, and then reducing said propionate to said propanal by contacting said propionate with metal hydride; and
(c) reacting the product of step (b) with an alkylidene trisubstituted phosphorane and then treating the resulting product with base, then formaldehyde, so as to produce said compounds.

4. A process of preparing compounds of the structure

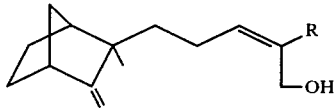

wherein R may be hydrogen or lower alkyl which comprises:
(a) preparing β-(3-exo-hydroxy-endo-2,3-dimethyl-2-norbornyl)-propionic acid δ-lactone by the process of claim 1;
(b) contacting the product of step (a) with a reagent selected from the group comprising ammonia, amines and metal amides to form β-(3-exo-hydroxy-endo-2,3-dimethyl-2-norborny)-propionamide, dehydrating said propionamide to form β-(endo-2-methyl-3-methylene-2-norbornyl)-propionitrile, and contacting said propionitrile with metal hydride to form β-(2-endo-methyl-3-methylene-2-norbornyl)-propanal; and
(c) reacting the product of step (b) with an alkylidene trisubstituted phosphorane and then treating the resulting product with base, then formaldehyde, so as to produce said compounds.

5. A process of preparing compounds of the structure:

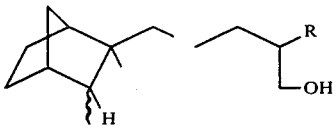

wherein R may be hydrogen or lower alkyl which comprises preparing compounds of the structure

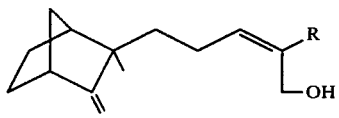

according to the processes of claim 3 or of claim 4 and then catalytically hydrogenating said compounds.

6. A process of preparing a compound having the structure:

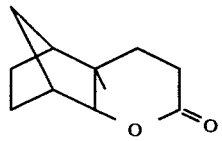

which comprises:
(a) preparing β-(2-exo-hydroxy-3,3-dimethyl-2-norbornyl)-propionic acid γ-lactone and its endo isomer from camphene by oxidizing camphene to form camphene epoxide and then reacting camphene epoxide with an anion having the formula ⊖CHXY wherein X may be hydrogen, ester, nitrile or carboxylate anion and wherein Y may be ester, nitrile or carboxylate anion; and
(b) treating the product of step (a) in accordance with the process of claim 1.

7. A process of preparing a compound having the structure

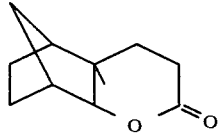

which comprises:
(a) reacting camphene with manganese triacetate or a haloacetic acid in the presence of an alkali metal halide; and
(b) treating the product of step (a) in accordance with the process of claim 1.

* * * * *

UNITED STATES PATENT AND TRADEMARK OFFICE
CERTIFICATE OF CORRECTION

PATENT NO. : 4,267,111
DATED : May 12, 1981
INVENTOR(S) : Brian J. Willis, Philip A. Christenson and Derek H.R. Barton It is certified that error appears in the above-identified patent and that said Letters Patent are hereby corrected as shown below:

At Column 4, between lines 20 and 25, the compounds should be as follows:

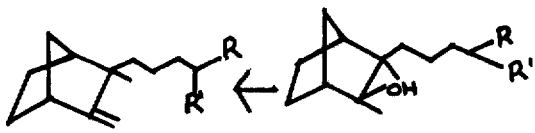

At Column 5, between lines 10 and 15, the compounds should be as follows:

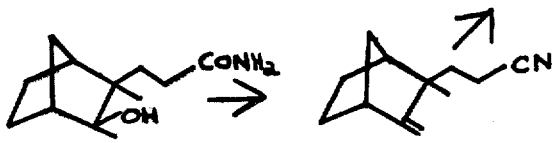

At Column 6, line 51 "qualacwood" should be --quaiacwood--.

UNITED STATES PATENT AND TRADEMARK OFFICE
CERTIFICATE OF CORRECTION

PATENT NO. : 4,267,111

DATED : May 12, 1981

INVENTOR(S) : Brian J. Willis, Philip A. Christenson and Derek H.R. Barton

It is certified that error appears in the above—identified patent and that said Letters Patent are hereby corrected as shown below:

At Column 12, between lines 27 and 40, the formulae should read as follows:

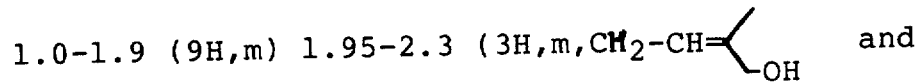

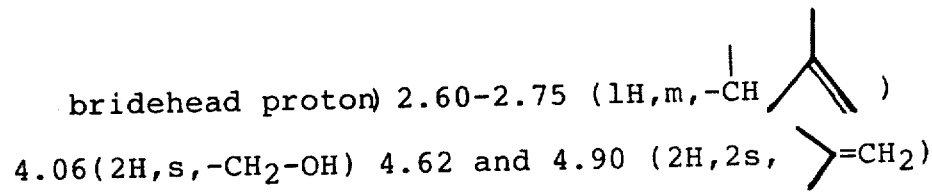

UNITED STATES PATENT AND TRADEMARK OFFICE
CERTIFICATE OF CORRECTION

PATENT NO. : 4,267,111

DATED : May 12, 1981

INVENTOR(S) : Brian J. Willis, Philip A. Christenson and Derek H.R. Barton

It is certified that error appears in the above-identified patent and that said Letters Patent are hereby corrected as shown below:

At Column 16, between lines 12 and 18, the compound should appear as follows:

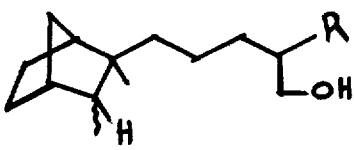

At Column 16, between lines 33 and 40, the compound should appear as follows:

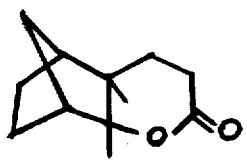

UNITED STATES PATENT AND TRADEMARK OFFICE
CERTIFICATE OF CORRECTION

PATENT NO. : 4,267,111
DATED : May 12, 1981
INVENTOR(S) : Brian J. Willis, Philip A. Christenson and Derek H.R. Barton It is certified that error appears in the above-identified patent and that said Letters Patent are hereby corrected as shown below:

At Column 16, between lines 55 and 61, the compound should appear as follows:

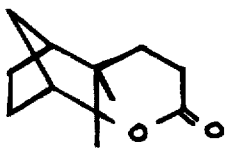

Signed and Sealed this

Sixth Day of September 1983

[SEAL]

Attest:

Attesting Officer

GERALD J. MOSSINGHOFF
Commissioner of Patents and Trademarks

UNITED STATES PATENT AND TRADEMARK OFFICE
CERTIFICATE OF CORRECTION

PATENT NO. : 4,267,111

DATED : May 12, 1981

INVENTOR(S) : Brian J. Willis, Philip A. Christenson and Derek H.R. Barton

It is certified that error appears in the above-identified patent and that said Letters Patent is hereby corrected as shown below:

At Column 4, between lines 20 and 25, the compounds should be as follows:

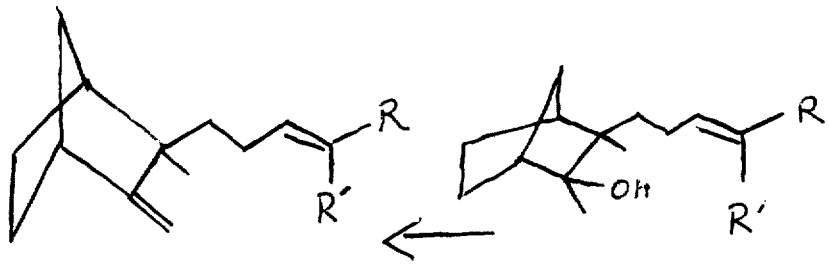

Signed and Sealed this

Thirteenth Day of March 1984

[SEAL]

Attest:

GERALD J. MOSSINGHOFF

Attesting Officer

Commissioner of Patents and Trademarks